US006957096B2

(12) United States Patent
Sfez et al.

(10) Patent No.: US 6,957,096 B2
(45) Date of Patent: Oct. 18, 2005

(54) METHOD AND APPARATUS FOR IMAGING ABSORBING OBJECTS IN A SCATTERING MEDIUM

(75) Inventors: Bruno Gad Sfez, Jerusalem (IL); Erel Granot, Tel Aviv (IL); Aner Lev, Modiin (IL); Zvi Kotler, Tel Aviv (IL)

(73) Assignee: The State of Israel, Atomic Energy Commission, Soreq nuclear Research Center, Yavne (IL)

( * ) Notice: Subject to any disclaimer, the term of this patent is extended or adjusted under 35 U.S.C. 154(b) by 33 days.

(21) Appl. No.: 10/470,385
(22) PCT Filed: Jan. 23, 2002
(86) PCT No.: PCT/IL02/00063

§ 371 (c)(1),
(2), (4) Date: Jan. 7, 2004

(87) PCT Pub. No.: WO02/059580

PCT Pub. Date: Aug. 1, 2002

(65) Prior Publication Data

US 2004/0127782 A1 Jul. 1, 2004

(30) Foreign Application Priority Data

Jan. 28, 2001 (IL) ................................................. 141135

(51) Int. Cl.⁷ ................................................. A61B 5/05
(52) U.S. Cl. ....................................................... 600/407
(58) Field of Search ............................... 600/407–476; 356/337

(56) References Cited

U.S. PATENT DOCUMENTS

| 5,070,455 | A | | 12/1991 | Singer et al. | |
|---|---|---|---|---|---|
| 5,528,365 | A | | 6/1996 | Gonatas | |
| 5,606,969 | A | * | 3/1997 | Butler et al. | 600/407 |
| 5,746,211 | A | * | 5/1998 | Leigh et al. | 600/407 |
| 6,041,248 | A | | 3/2000 | Wang | |

OTHER PUBLICATIONS

M. Kempe et al, "Acousto–Optic Tomography with Multiply Scattered Light," Optical Society of America, vol. 14, No. 5, May 1997, pp. 1151–1158.

Shechao Charles Feng et al, "Analytical Perturbation Theory of Photon Migration in the Presence of a Single Absorbing or Scattering Defect Sphere," SOIE, vol. 2389, pp. 54–63, 1995.

Akira Ishimaru, "Wave Propagation and Scattering in Random Media," Academic Press, 1978, pp. 175–179.

S.J. Matcher et al, "Absolute Quantification Methods in Tissue Near Infrared Spectroscopy," SPIE, vol. 2389, 1995, pp. 486–495.

Aner Lev et al, "Ultrasonic Probing of the Banana Photon Distribution in Turbid Media," vol. 4256, Jan. 2001, pp. 233–240.

A. Lev et al, "Ultrasound Tagged Light Imaging in Turbid Media in Reflectance Geometry," Optics Letters, vol. 25, No. 6, Mar. 15, 2000, pp. 378–380.

(Continued)

Primary Examiner—Ali Imam
(74) Attorney, Agent, or Firm—Browdy and Neimark P.L.L.C.

(57) ABSTRACT

A method and processing device are presented for reconstructing an absorption and/or scattering image of a region of interest inside a scattering medium. A mathematical model is provided being representative of a relation between the distribution of the intensity and phase of electromagnetic radiation components scattered from a medium and a certain attenuation factor, which is function of spatial variations of scattering and absorption coefficients of the medium. The mathematical is used for processing a map of distribution of the intensity of electromagnetic radiation components scattered from known locations within the region of interest, thereby producing a halftone pattern of the region of interest.

28 Claims, 5 Drawing Sheets

OTHER PUBLICATIONS

Simon R. Arridge et al, "Optical Imaging in Medicine: II. Modelling and Reconstruction," Physics in Medicine and Biology vol. 42, 1997, pp. 841–853.

Valery Tuchin, "Tissue Optics: Light Scattering Methods and Instruments for Medical Diagnosis," Tutorial Texts in Optical Engineering, vol. TT38, 2000, p. 9.

* cited by examiner

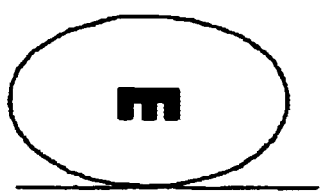
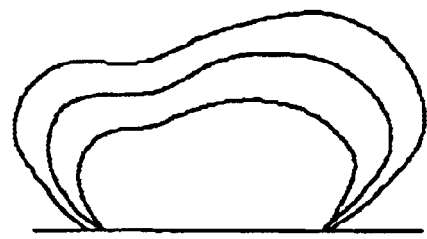
FIG. 3A            FIG. 3B (PRIOR ART)
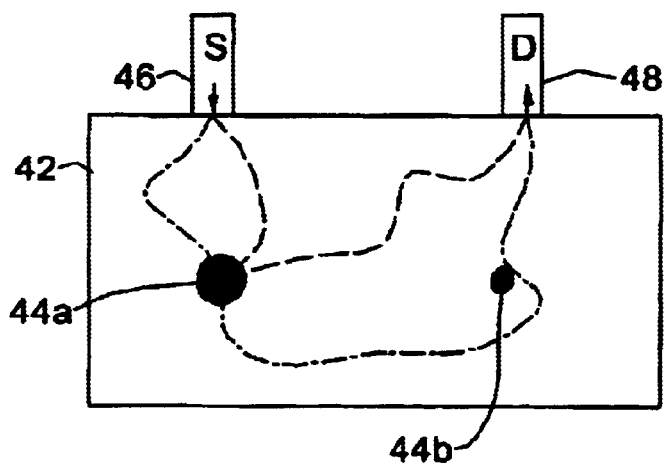
FIG. 4

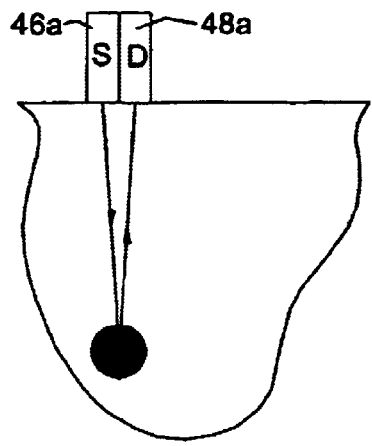
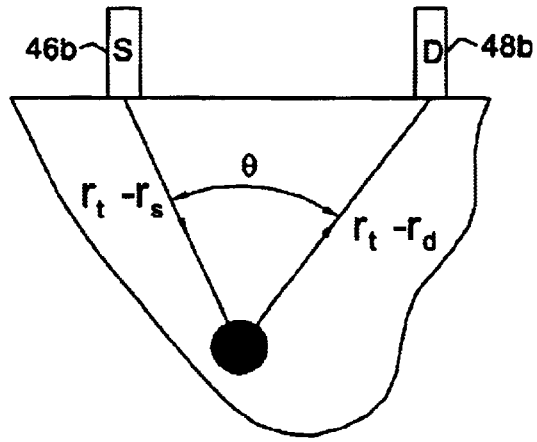
FIG. 5A    FIG. 5B
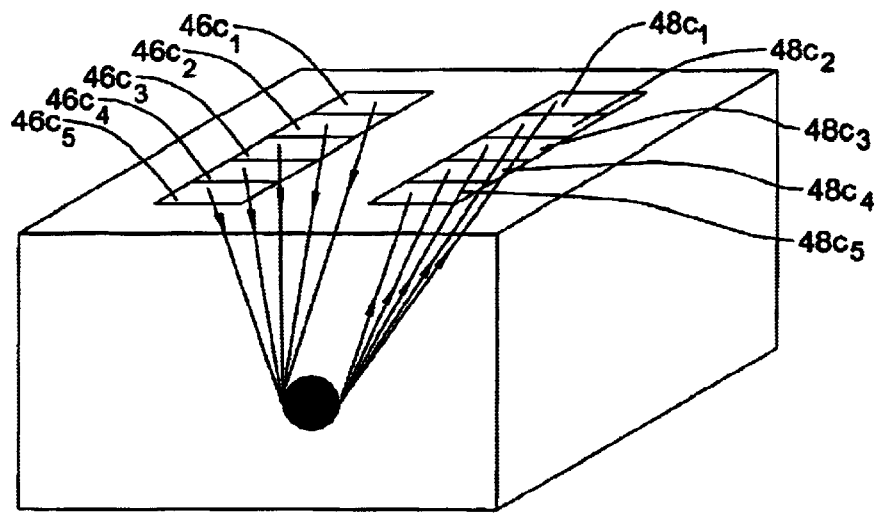
FIG. 5C

METHOD AND APPARATUS FOR IMAGING ABSORBING OBJECTS IN A SCATTERING MEDIUM

FIELD OF THE INVENTION

This invention is generally in the field of imaging techniques, and relates to a method and apparatus for real-time imaging of absorbing objects within a scattering medium. The invention utilizes ultrasound tagging of light, and is particularly useful for non-invasive detection/ measurements of absorbing agents, such as hemoglobin, in biological tissues.

BACKGROUND OF THE INVENTION

In recent years, much effort has been devoted to map the inside of diffusive bodies using ultrasound and electromagnetic waves. If a sound (or ultrasound) wave is located inside a scattering medium and concurrently a continuous electromagnetic wave (such as a laser light beam) crosses said medium and is strongly diffused thereby, the electromagnetic wave frequency is shifted by the sound frequency (acousto-optic effect) at the location of the sound (or ultrasound) wave, while in the other regions, the frequency of the light is unchanged. The electromagnetic waves with the shifted or tagged frequencies are detected. Since the location of the ultrasound waves inside the medium, and consequently, the locations of interaction between the ultrasound and electromagnetic waves can easily be determined, a 3-D representation of the medium can be obtained.

Lev A. et al. "Ultrasound probing of the banana photon distribution in turbid media", Biomedical Optoacoustics II, San Jose, Calif., USA, 23–24 Jan. 2001, vol. 4256, pp. 233–240 discloses the possibility of ultrasound tagging of light to map the photon density inside solid turbine media. The modulation of the optical field transmitted through a scattering medium by an ultrasound beam is also disclosed in M. Kampe et al. "Acousto-optic tomography with multiply scattered light", Optical Society of America, 1997, pp. 1151–1158.

It has been shown [Optics Letters, Lev et al, March 2000] that the technique of ultrasound tagging of light provides for locating an electromagnetic wave absorbing object within a non-absorbing, diffusive medium. However, it appears that when the are several absorbing objects or the single object has a pattern of absorbing locations within the diffusive medium, a correlation between the absorption of the different objects/locations occurs, and the so-obtained 3-D representation is insufficient to provide an exact picture of the absorbing pattern within the medium, and data reconstruction is thus required.

Image reconstruction techniques typically used with optical measurements utilize inverse scattering algorithms [S. R. Arridge and J. C. Hebden, "Optical imaging in medicine II. Modeling and reconstruction", Physics in Medicine and Biology 42, 841–853 (1997)]. In these methods light scattered from the medium is detected enabling a two dimensional data representation. This two-dimensional data is then reconstructed into a three-dimensional pattern of absorption (or scattering). The results of such techniques are limited by several factors: the optical measurement methods are very sensitive to boundary conditions (sensors or sources positions), the data reconstruction requires long computation time, and the image resolution is relatively low, e.g., general not exceeding 5 mm in the case of optical tomography.

SUMMARY OF THE INVENTION

There is accordingly a need in the art to enable 2D or 3D imaging of am absorbing pattern within a light scattering medium, by providing a novel method and apparatus for acquiring data representative of the intensity distribution of the light response at known locations (voxels) inside the scattering medium, and processing these data to reconstruct the image including an absorbing and/or scattering patter in this medium.

The present invention takes advantage of the acoustic tagging of the light technique enabling identification of the locations inside the medium corresponding to the detected scattered light components. In other words, irradiation of the medium with acoustic waves is used solely for the purpose of mapping the detected scattered light components. The acoustic tagging of light provides for obtaining the 3-D representation (map) of the medium in real-time. Although this representation by itself is indicative of the location of an absorbing region, it does not provide for identifying the absorbing pattern within this region (inter alia, because of the cross talk between the different paths that light tends to take within the patterned region).

The main idea of the present invention consists of providing an image (halftone pattern) of absorbing and/or scattering inhomogenenities inside the scattering medium by processing the map (pattern) of the detected light signal (e.g., associated with the locations of interaction between acoustic and electromagnetic waves). To this end, the map of the detected light signals is considered as a function of the attenuation factor, which, in turn, depends on both the scattering and absorption properties. In other words, the attenuation factor is representative of the changes in the detected light intensity pattern scattered from a scattering medium caused by the absorbing pattern thereinside and/or by spatial variations of the scattering properties of the medium.

To achieve the above, the measured intensity pattern $\gamma(r_1)$ for each position t inside the medium (e.g., tagged location) is, on the one hand, related to the absorption and scattering coefficients at that location, and, on the other hand, related to the diffusion properties of the medium defined by the photons propagation inside the medium. These two relations provide the basis of the reconstruction algorithm according to the invention.

The attenuation factor $\mu(r_1)$ is given by:

$$\mu = \sqrt{3\mu_a(\mu'_s + \mu_a)}$$

wherein $\mu_a$ is the absorption coefficient, and $\mu'_s$ is the reduced scattering coefficient ["Tissue Optics" V. Tuchin, SPIE Press (2000)].

If the scattering coefficient does not change drastically from one point to another, the determination of the attenuation factor is directly related to the absorption coefficient. In the cases where the scattering coefficient varies drastically in space, both coefficients should be determined independently.

The present invention also takes into consideration the relative locations of the light source and detector with respect to each other, as well as the number of sources and detectors used in the measuring device.

Thus, according to one aspect of the present invention, there is provided a method of reconstructing an image of a region of interest inside a scattering medium, the method utilizing a map of distribution of the intensity of electromagnetic radiation components scattered from tagged locations in said region of interest, said map corresponding to certain relative positions of at least one source of the electromagnetic radiation (14) and at least one detector (16) of the scattered electromagnetic radiation with respect to one another and with respect to the tagged locations inside the medium, the method being characterized in that:

data indicative of said relative positions of the at least one electromagnetic radiation source and at least one scattered radiation detector is utilized to provide a mathematical model that presents a relation between a map of distribution of the intensity of electromagnetic radiation components γ scattered from tagged locations in a medium and a halftone map of an attenuation for $\mu(r)$, which is a function of spatial variations of scattering and absorption coefficients of the medium, said relation being indicative of a degree of inhomogeneity of at least one of the scattering and absorption coefficient within the medium; and, said mathematical model is utilized for processing the map of the distribution of the electromagnetic radiation components to thereby obtain a halftone pattern of said region of interest.

According to another aspect of the present invention, there is provided a processing device for use with a measuring apparatus which is operable to detect the intensity of light scattered from tagged locations in a scattering medium, the processing device comprising inter alia a memory utility for storing a data indicative of relative positions of at least one light source and at least one detector with respect to one another and with respect to the tagged locations inside the medium as used in said measuring apparatus, and comprising a data processing and analyzing utility for processing input data and generating data indicative of the processing results, the processing device being characterized in that:

said processing device is operable to utilize said data indicative of the relative positions to create a predetermined mathematical model and store it in the memory utility, said mathematical model presenting a relation between a map of the measured intensities distribution γ and a halftone map of a certain attenuation factor $\mu(r)$, which is a function of the spatial variation of scattering and absorption coefficients of the medium, said relation being indicative of a degree of inhomogeneity of at least one of the scattering and absorption coefficients within the medium; and said data processing and analyzing utility, is responsive to input data, coming from the measuring apparatus and being indicative of a map of distribution of the intensity of light scattered from the tagged locations within said region of interest, to apply said mathematical model to said measured data, and thereby obtain a halftone pattern of the region of interest.

There is also provided according to yet another aspect of the invention, an apparatus for imaging a region of interest in a scattering medium, the apparatus comprising:

(i) a measuring apparatus operable to measure electromagnetic radiation components scattered from different identifiable locations inside the region of interest, and generate measured data indicative of a map of the intensity distribution of the electromagnetic radiation within the region of interest; and (ii) a processing device having a memory unit for storing a predetermined mathematical model presenting theoretical data representative of a relation between distribution of the intensity of electromagnetic radiation scattered from a scattering medium and a certain attenuation factor, which is a function of the spatial variations of scattering and absorption coefficients of the medium; and a processing utility responsive to input data including said measured data and preprogrammed to process the measured data with the mathematical model to thereby obtain a halftone pattern of the region of interest and enable imaging of the region of interest.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 3A and 3B schematically illustrate the conventional imaging technique utilizing the ultrasound tagging of light;

FIG. 4 schematically illustrates the cross-talk problem to be solved by the present invention;

FIG. 5A to 5C schematically illustrates three possible examples of an electromagnetic source/detector arrangement suitable to be used in the present invention;

DETAILED DESCRIPTION OF THE INVENTION

Figure 1:
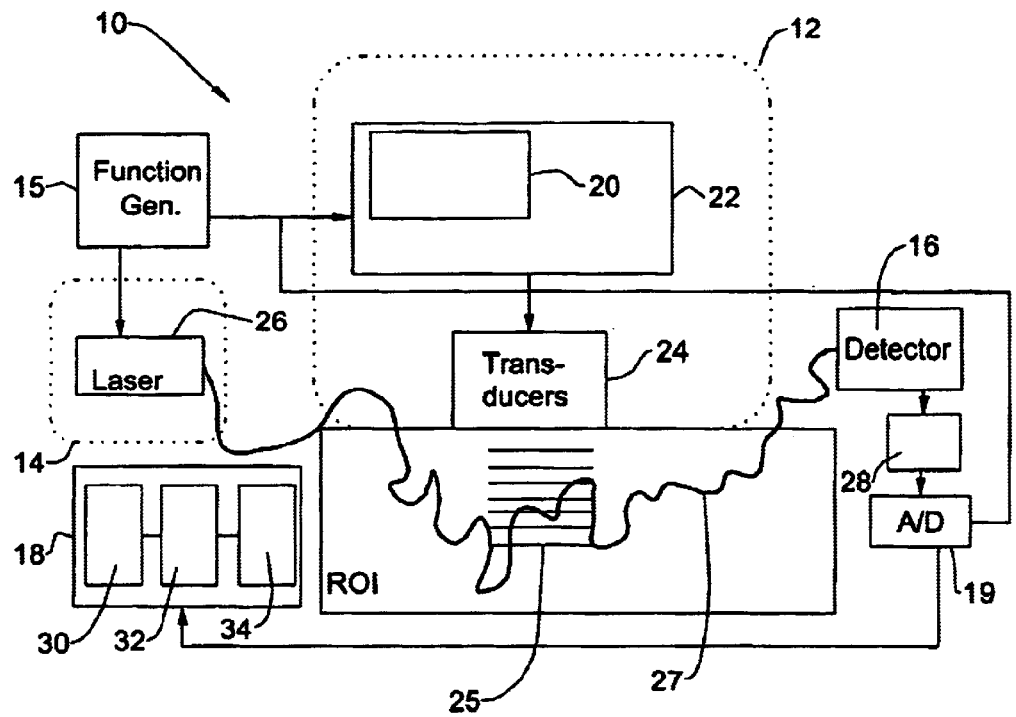
FIG. 1 is a schematic illustration of an exemplary apparatus constructed and operated for imaging a region of interest by ultrasound tagging of light, which is suitable to be used for the purposes of the present invention.

Referring to FIG. 1, there is illustrated a measurement apparatus 10 for obtaining a map of intensity of the distribution of light scattered from a plurality of known locations with a region of interest (ROI) in a scattering medium (for example, biological tissue) utilizing ultrasound tagging of light. The apparatus 10 comprises such main constructional parts as an ultrasound (generally, acoustic) unit 12 coupled to the medium, an illuminator 14 (constituting an electromagnetic radiation source) optically coupled to the medium, a detector 16, whose output is connectable to a control unit 18. The apparatus 10 also comprises a phase and frequency control utility 20, which, in the present example, is associated with the ultrasound unit 12, which comprises an acoustic or ultrasound generator 22 (possibly including an electronic beam forming unit and an array of amplifiers), and a transducer arrangement 24. The operation of the ultrasound unit 12 is aimed at delivering the proper ultrasound wave within the region of interest in the medium.

A function generator 15 operates the ultrasound unit 12 and an analog-to-digital-converter (card) 19 via a triggering signal TS. Concurrently, the generator 22 transmits an electrical signal to the transducer arrangement 24 through the phase control utility 18 to thereby actuate one or more transducers to transmit, respectively, one or more ultrasound signals 25 into a region of interest in the medium.

The illuminator 14 comprises one or several laser devices 26 generating incident radiation of at least one wavelength (for example, in a range of 690–900 nm in order to detect hemoglobin in biological tissue), which propagates towards the region of interest. Laser light is diffused (scattered) by the medium, and the diffused light 27 interacts with the ultrasound wave 25, and the detector 16 detects the signal resulting from this interaction. The electric output of the detector 16 is directed to the analog-to-digital converter through a band-pass filter and amplifier 28, to thereby produce corresponding digital signals received by the control unit 18.

The control unit 18 comprises a processing devices 30 and 32, and a display 34 for displaying an image of the region of interest. The processing device 30 is pre-programmed to process and analyze the data received from the detector 16 in the conventional manner, namely, by applying a power spectrum operation to the measured data and identifying variations in light intensity at different frequencies, to thereby generate measured data indicative thereof. The operational principles of the processor 30 do not form part of the present invention, and therefore need not be described in detail. The processing device 32 is connectable to the output of the device 30 for further processing the measured data according to the invention.

Figure 2:
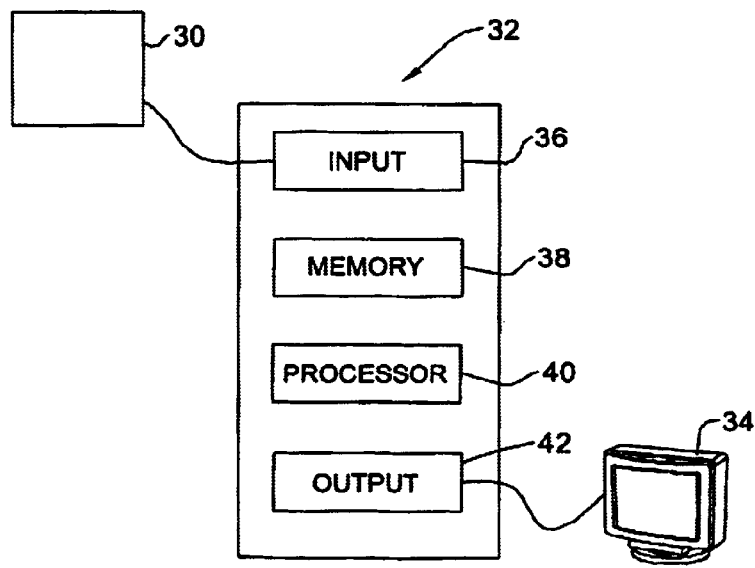
FIG. 2 more specifically illustrates a processing device according to the invention used with the apparatus of FIG. 1.

As shown in FIG. 2, the processing device 32 is typically a computer device comprising a data input utility 36 for receiving the measured data from the processor 30, a memory utility 38, a data processing and analyzing utility 40, and a data output utility 42 connectable to the display 34 and/or any other data presenting or data transmitting utility. The memory utility 38 stores a predetermined mathematical model, and the utility 40 is preprogrammed to process the measured data with the mathematical model, as will be described further below.

It should be understood that input and output data may be of the kind to be transmitted through wires or wireless to other devices. The input and output utilities are constructed accordingly. It should also be understood that the processing device 32 can be a separate unit connectable to the measurement apparatus 10 that includes the control unit 18 with the processor 30 as its constructional part.

Turning back to FIG. 1, it should be noted that the phase control utility 20 may be alternatively associated with the illuminator 14, and may be a part of the function generator 15. In this case, the function generator operates to modulate the output intensity of the laser using a phase modulation scheme. The measurement device may be of any known kind, for example as disclosed in U.S. Pat. No. 6,041,248, and is disclosed in the co-pending application assigned to the assignee of the present application. The construction and operation of the measurement device do not form part of the present invention, and therefore are not specifically described, except to note the following:

The interaction between the light wave and the ultrasound results in that the frequency/phase of light is shifted by the frequency/phase of the ultrasound, and the presence of an absorbing agent in the scattering medium can be determined from the change in the intensity distribution of the frequency/phase shifted light signals. The light source, the probed region, and the detector do not have to be specifically aligned with each other, and can have any geometric configuration, provided that enough photons reach the detector. This allows multiple-source/detector configurations, with an increase in the signal to noise ratio and better light filling of the tissues.

The interaction is as follows: The light source emits light of frequency $\omega$ into the probed region (region of interest). The ultrasound pulses of frequency $\Omega US$ are transmitted into the probed region. The current location(s) of the interaction in the X-Y plane is defined by the current location of the transducer(s), and along the Z-axis by the phase of ultrasound pulses. The ultrasound modulated light having a shifted frequency $\omega+\Omega US$, and non-modulated light having the frequency $\omega$ are received by the detector, which mixes them and generates a signal modulated at the ultrasound frequency. Data indicative of the detected signals is processed in the device 30 to obtain the measured data in the form of a map of the modulated light intensity distribution within the region of interest.

It should be noted that the present invention is not limited to the above-described technique of obtaining data representation (e.g., 3D representation) of the scattered light map. Any other suitable technique and device can be used for obtaining such measured data to be further processed by the present invention. For example, the technique of the above-indicated U.S. Pat. No. 6,041,248 is suitable.

FIG. 3A schematically illustrates a region of interest (ROI), which is a scattering medium (e.g., biological tissue), and which has an absorbing region (AR) thereinside. FIG. 3B schematically illustrates the measured data (MD) obtained with the processor 30. The measured data is the light intensity map typically shaped like a banana between the source and the detector [S. C. Feng, F. Zeng and B. Chance, SPIE Vol. 2389,pp 54–63. 1995], and is distorted by the presence of the absorbing region. It is thus evident that in order to obtain a halftone pattern (image) of the absorbing region, further processing of the measured data is needed.

The ultrasound tagging of light allows to obtain a data representation of the region of interest (e.g., three-dimensional representation). However, these data do not give rise directly to the absorption distribution (pattern) because of the cross talk between the different paths that photons can take. This is illustrated in FIG. 4, showing a region of interest 42 in a scattering medium having two spaced-apart absorbers 44a and 44b. Photons generated by a light source 46 propagate through the region of interest in two photon paths towards a detector 48. Although a separate tagging zone is located at the absorber 44b, the photons crossing the absorber 44a will influence the tagged signal of the absorber 44b at the detector. Thus there is a need for a reconstruction method that will enable to eliminate these cross-talk effects.

According to the invention, the data reconstruction method is based on considering the measured intensity pattern $\gamma(r_t)$ for each position t of the tagging location, as a function of the attenuation factor $\mu(r_t)$. The latter depends on both the scattering and absorption properties of the region of interest, and is actually representative of the changes in the detected light intensity pattern caused by the absorbing pattern in the region of interest. Hence, the measured intensity pattern $\gamma(r_t)$ for each tagged location t is, on the one hand, related to the absorption coefficient at that location, and, on the other hand, related to the diffusion properties of the medium defined by the light propagation inside the medium.

The attenuation factor is determined as follows:

$$\mu = \sqrt{3\mu_a(\mu'_s+\mu_a)}$$

wherein $\mu_a$ is the absorption coefficient and $\mu'_s$ is the reduced scattering coefficient.

If the scattering coefficient does not change drastically from one location to another, the determination of the attenuation factor is directly related to the determination of the absorption coefficient. In the medium of the kind where the scattering coefficient varies drastically in space, both the absorption and scattering coefficients should be determined independently. In the case of brain trauma or stroke, or in the case of cancer detection based on the angiogenesis process, the effect of variations in the absorption pattern of the medium due to the presence of blood vessels is much more dominant than that of the variations in the scattering properties. Therefore, in that case, the effect of changes in scattering properties within the medium can generally be neglected. As for effects in bones for examples, the scattering coefficient's variations between the locations of the cortical bone and the trabecular bone, or between the locations of the sane and diseased bones (e.g., in the case of osetoporosis), are quite important. Accordingly, in these cases, changes in scattering properties should also be taken into consideration.

It is known [A. Ishimaru, "Wave Propagation and Scattering in Random Media", Academic Press, (1978)] that electromagnetic waves' propagation in scattering media can be considered (in a first but well-established approximation) as experiencing a diffusion process (the so-called $P_1$ approximation). Therefore, a diffusion equation for the photons' number (or equivalently, the photon or energy density) considering the attenuation factor along three orthogonal axes is as follows:

$$(\nabla^2 - \mu^2(r))U(r) = S(r) \quad (1)$$

wherein $U(r)$ is the intensity of the scattered light (electromagnetic wave); $S(r)$ characterizes the sources distribution (i.e., the distribution of the illuminating intensity); and $\mu(r)$ is the attenuation factor or the so-called extinction coefficient.

As indicated above, when the light with a frequency $\omega$ interacts with the ultrasound (acoustic) beam of a frequency $\Omega$, a new frequency $\omega+\Omega$ is created (with a certain tagging efficiency $\eta$). This, however, does not affect the scattering properties of the medium, and thus the diffusion equation (1) remains the same.

Turning back to FIG. 4, let us consider the following geometric configuration: the light source 46 is located at the surface location $r_s$, the detector 48 is located at $r_d$, and the ultrasound beam is located at $r_t$ inside the medium. Here, the index "t" denotes the tagging zone, namely, the location in the region of interest where light frequency is modulated.

The probability for a photon to migrate from the first location $r_1$ to the second location $r_2$ is denoted by $\Gamma(r_1, r_2)$. The probability to detect a modulated photon is proportional to the product of the probability to migrate from the source to the tagging zone, the tagging efficiency (defined as the percentage of photons crossing the ultrasound wave that effectively get tagged), and the probability to migrate from the tagging zone to the detector. The tagging efficiency is defined as the percentage of photons crossing the ultrasound wave that effectively get tagged Therefore, the detected light intensity distribution $\gamma(r_t)$ is as follows:

$$\gamma(r_t) \approx \Gamma(r_s, r_t)\Gamma(r_t, r_d)\eta S_0 \quad (2)$$

wherein $S_0$ is the source intensity (i.e., the intensity of the incident light).

In the above equation, intensity of photons that several times interacted with the acoustic waves has been neglected, since the proportion scales of these photons is small.

In general, when the detector, the source and the tagging zone are all localized in three different points, the probabilities $\Gamma$ are reduced to the Green function $G(r)$ of the equation (1), that is $$\gamma(r_t) \approx (2\pi)^2 G(r_s - r_t) G(r_t - r_d) \eta S_0 \quad (3)$$

In the general case, where the light source is not a point source and/or the detector is not a point detector, the above equation (3) must be replaced by the following:

$$\gamma(r_t) = \eta j_0 \int\int dA_s dA_d \Gamma(r_s, r_t)\Gamma(r_t, r_d) = \eta S_0 \Gamma_s(r_t)\Gamma_d(r_t) \quad (4)$$

wherein $A_s$ and $A_d$ represent, respectively, the source and detector area, and $\Gamma_s(r_t)$ and $\Gamma_d(r_t)$ are the probabilities of the photon to migrate from, respectively, the source to the tagging location $r_t$ and from the tagging location $r_t$ to the detector. It should be noted that since $\Gamma(r_1, r_2) = \Gamma(r_2, r_1)$, the probability $\Gamma_d(r_t)$ could also be referred to as the probability of the photon to migrate from the detector to the tagging location $r_t$.

Accordingly, we have:

$$\frac{\nabla^2 \sqrt{\gamma}}{\sqrt{\gamma}} = -\frac{1}{4}\left[\frac{\nabla \Gamma_s}{\Gamma_s} - \frac{\nabla \Gamma_d}{\Gamma_d}\right]^2 + \frac{1}{2}\left[\frac{\nabla^2 \Gamma_s}{\Gamma_s} + \frac{\nabla^2 \Gamma_d}{\Gamma_d}\right] \quad (5)$$

The above equation (5) is an exact algebraic relation without any hidden physical assumption, and is therefore always valid.

As there is no light source inside the medium, both probabilities $\Gamma_s(r_t)$ and $\Gamma_d(r_t)$ are solutions of the diffusion equation (1) for any location $r_t$ inside the medium, but without the source-associated term:

$$\nabla^2 \Gamma(r_t) = \mu^2(r_t)\Gamma(r_t) \quad (6)$$

Hence, equation (5) can be rewritten as follows:

$$\frac{\nabla^2 \sqrt{\gamma}}{\sqrt{\gamma}} = -\frac{1}{4}\left[\frac{\nabla \Gamma_s}{\Gamma_s} - \frac{\nabla \Gamma_d}{\Gamma_d}\right]^2 + \mu^2(r_t) \quad (7)$$

wherein all the derivatives are taken with respect to the tagged locations $r_t$. From this point of view, the only approximation that leads to equation (7) is the equation (2), i.e., the multiplication assumption.

Reference is now made to FIGS. 5A–5C, illustrating three possible examples of an electromagnetic source/detector arrangement.

In the example of FIG. 5A, the source 46A and the detector 48A are at the same location and have the same dimensions. In this case, equation (7) can be simplified and yields the following:

$$\frac{\nabla^2 \sqrt{\gamma(r_t)}}{\sqrt{\gamma(r_t)}} = \mu^2(r_t) \quad (8)$$

In the example of FIG. 5B, the source and the detector 46B and 48B are spaced from each other, and a certain angle $\theta$ therefore exists between the vectors $(r_t - r_s)$ and $(r_t - r_d)$ presenting the central axes of incident and scattered light components propagating to and from the absorbing tagged region AR. In this case, the second term in the equation (5) above cannot be neglected any more and must be estimated. In the second order approximation, we can evaluate $\Gamma$ as if the medium is homogenous. In that case, the analytical expression of $\Gamma$ is well-known [A. Ishimaru, "Wave Propagation and Scattering in Random Media", Academic Press, (1978)] and therefore the expression $$\frac{\nabla \Gamma}{\Gamma}$$

can be developed in powers of $1/r$. For distances $r$ which are larger than $1/\bar{\mu}$, $\bar{\mu}$ being the average value of the attenuation factor $\mu(r)$, we have the general expression:

$$\frac{\nabla \Gamma}{\Gamma}(r) \sim -\mu(r)\frac{r}{|r|} - \frac{r}{|r|^2} \qquad (9)$$

and therefore:

$$\frac{\nabla^2 \sqrt{\gamma}}{\sqrt{\gamma}} \cong \mu^2(r_t)\frac{[1+\cos\theta]}{2}$$

It should be understood that in equation (9), r represents any position in the medium, and therefore states a physical approximation that is not linked with the ultrasound tagging of light. In the last equation, the value of r is replaced by $r_t$, thereby taking into account the ultrasound tagging.

In the case of spaced-apart source and detector, the image obtained at the detector should not be drastically different from that obtained with the source and detector located adjacent to each other. Therefore, equation (8) should just be corrected as presented in the last equation. This correction is estimated by taking the solution of the problem as if the medium is homogenous, and is added to equation (8).

Therefore, equation (8) can be generalized to the case where the source and the detector are at different places, as follows:

$$\mu^2(r_t) = \frac{2}{1+\cos\theta}\frac{\nabla^2\sqrt{\gamma}}{\sqrt{\gamma}} \qquad (10)$$

Equation (10) returns to equation (8) when $\theta \to 0$, namely when the distance between the source and the detector is much smaller than the distance between the source/detector and the tagging zone (the acoustic wave).

FIG. 5C exemplifies the situation with an array of sources $46C_1$–$46C_5$ (generally at least two) and an array of detectors $48C_1$–$48C_5$ (similarly, at least two detectors). This case is the most general, and requires an iterative algorithm consisting of estimating the light intensity detected by each detector considering that this detected light intensity is produced by scattered light components of all the sources. Thus, the iterative algorithm includes the following steps:

Step 1: Equivalent location of the source $r_s$ is evaluated as follows:

$$r_s = \frac{\sum_{j=1}^{N_s} S_j r_j}{\sum_{j=1}^{N_s} S_j} \qquad (11)$$

wherein $S_j$ is the intensity of the $j^{th}$ source at the location $r_j$.

From the above-described example of FIG. 5B, $\mu^{(i)}(r_t)$ being the first approximation of $\mu(r_t)$ can be evaluated using the following equation:

$$+2d\mu^{(1)}(r_t) = \frac{1}{N_d}\sum_{i=1}^{N_d}\frac{2}{1+\cos\theta_i}\frac{\nabla^2\sqrt{\gamma_{(i)}(r_t)}}{\sqrt{\gamma_{(i)}(r_t)}} \qquad (12)$$

wherein $N_d$ is the total number of detectors, $\gamma_{(i)}(r_t)$ is the light intensity returned from the tagging location $r_t$ to the $i^{th}$, and $\theta_i$ is the angle between the vectors $r_t-r_i$ and $r_t-r_s$.

Step 2: The diffusion equation (1) is solved using $\mu^{(1)}(r_t)$ instead of $\mu(r_t)$. To this end, two equations must be solved: one for the sources and one for the detectors. The boundary conditions must be chosen so as to match the sources and the detectors' arrangement:

$$-\nabla^2\Gamma_s^{(1)}(r) + \mu_{(1)}^2(r)\Gamma_s^{(1)}(r) = S(r) \qquad (13)$$

$$-\nabla^2\Gamma_d^{(1)}(r) + \mu_{(1)}^2(r)\Gamma_d^{(1)}(r) = S(r) \qquad (14)$$

Step 3: Now, the new value for $\mu(r_t)$, i.e., $\mu_{(2)}(r_t)$ is obtained using the following:

$$\mu_{(2)}^2(r_t) = \mu_{(1)}^2(r_t) + \frac{1}{4}\left[\frac{\nabla\Gamma_s^{(1)}}{\Gamma_s^{(1)}} - \frac{\nabla\Gamma_d^{(1)}}{\Gamma_d^{(1)}}\right]^2 \qquad (15)$$

Step 4: Steps 2 and 3 are repeated until a precise enough value for $\mu(r_t)$ is obtained. The repetitive process can for example proceed until the difference in the value of $\mu(r_t)$ from two consecutive iterations is smaller than $\epsilon$ (in absolute value).

The method of the present invention can be applied directly to the determination of biological tissues' saturation. By choosing two different wavelengths of incident light in the near-infrared spectral region (670 nm to 900 nm), it is possible to obtain the value of $\mu(r,\lambda)$ for both wavelengths. The absorption of such a medium is essentially due to oxyhemoglobin and deoxyhemoglobin, and the manner of extracting the oxygen saturation of tissues from the measured scattered light is known in the art. If scattering properties of the medium are not varying strongly from one place to another, the ratio of $\mu(r,\lambda_1)/\mu(r,\lambda_2)$ is directly proportional to the ratio $\mu_a(r,\lambda_1)/\mu_a(r,\lambda_2)$ [S. J. Matcher, P. Kirpatrick, K. Nahid, M. Cope and D. T. Delpy, SPIE Vol. 2389. pp 486–495, 1995]. This ratio leads directly to the saturation.

In some cases, the knowledge of the attenuation factor is insufficient for imaging purposes. As indicated above, such a situation occurs with a medium of the kind where the scattering coefficient varies drastically in space. In this case, both the absorption and the reduced scattering coefficients $\mu_a$ and $\mu'_s$ should be determined independently. More specifically, the spatial distribution of the scattering coefficient within the region of interest is to be determined.

Figure 6:
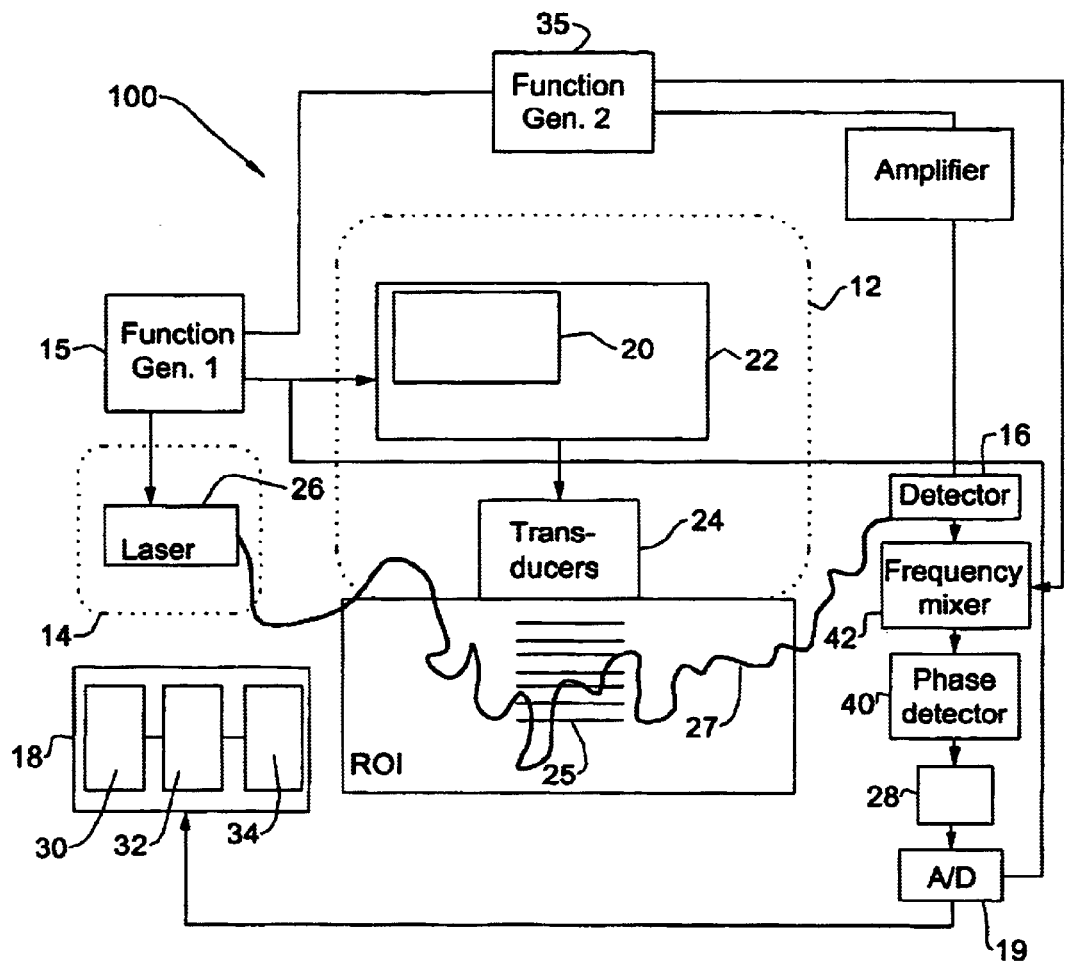
FIG. 6 schematically illustrates another example of a measurement device suitable to be used with the present invention.

The above can be implemented by using a measurement device somewhat different from the device of FIG. 1. This measurement device is schematically illustrated in FIG. 6, being generally denoted 100. To facilitate understanding, the same reference numbers are used for identifying those components which are common in the devices 10 and 100. Thus, in the device 100, there is additionally provided a function generator 35 that modulates the detector response and provides a synchronized reference, an amplifier 36 to amplify the signal to the detector, a phase detection system (e.g., a phase-lock loop or PLL) 40 and a frequency mixer system 42, which are connected to the detector and to the filter 28. It should be understood that the operations of the function generators 15 and 35 are appropriately synchronized. The operation of the measurement device 100 is based on irradiating the region of interest with a high-frequency modulated light, and detecting the phase variations in the ultrasound tagged light components, i.e., light components scattered from different locations of the region of interest. Thus, in this configuration, the detected light signals coming from different spatial coordinates, in addition to being frequency tagged due to the interaction with ultrasound, have certain phase tags, thereby enabling separate identification of the light intensity changes due to the changes in the scattering properties only.

More specifically, the laser is modulated at a high frequency (typically between 50 MHz and 1 GHz) at the modulation ω. This creates a so-called diffusive wave within the scattering medium ["Tissue Optics", V. Tuchin, SPIE Press (2000)]. The photomultiplier dynodes (detector) are also modulated at the frequency ω+δωl+Ω, wherein Ω is the ultrasound frequency. At the frequency δωl, the detected signal depends on the exact position of the ultrasound pulse inside the medium. The ultrasound pulse position determines the distance that the diffusive wave propagates, and therefore its phase. This phase is determined by comparing the signal at the frequency δωl with a reference signal at the same frequency (derived from the same clock as the generator that modulates the dynodes). It should be noted that the frequency ω is either fixed or time dependent. This is important in order to enable obtaining the relation between the ultrasound pulse position and the signal. It should also be understood that other frequency combinations could be used in order to obtain a similar result.

The knowledge of both the amplitude and phase of the detected signal gives the knowledge of the complex intensity of the signal. The amplitude can be determined by any known technique (e.g., U.S. Pat. No. 6,041,248) or by the technique of the above-indicated co-pending application utilizing measurement of the power spectrum. The time dependent equation is as follows:

$$-\nabla^2 U(r) + \mu^2(r)U(r) - \frac{1}{D}\frac{\partial U}{\partial t} = \frac{S(r)}{D} \quad (16)$$

wherein $$D = \frac{c}{3(\mu_a + \mu'_s)}$$

is the diffusion coefficient and c is the speed of light in vacuum.

The light source S is now considered as a modulated light source, rather than a static light source, as in the previously described examples, and therefore we have:

$$S(r,t)=S_0(r)\exp(-i(\omega t+\phi)) \quad (17)$$

The general form of the electromagnetic wave intensity is as follows:

$$U(r,t)=U_0(r,t)\exp(-i\omega t) \quad (18)$$

In that case the diffusion equation becomes:

$$(\nabla^2 - k^2)U_0(r,t) = -\frac{S_0(r)}{D}\exp(-i\varphi) \quad (19)$$

wherein the complex attenuation coefficient k is as follows:

$$k^2 = \mu^2 + i\frac{\omega}{D} \quad (20)$$

The above equation is conceptually similar to equation (2), and distinguished from equation (2) in the following: coefficient k replaces coefficient μ; all the values are complex, and therefore, not only the amplitude but also the phase of the detected signal ϕ is to be measured.

Once k is determined experimentally (both $k_r$ and $k_i$), equation (20) is a simple system of two equations with two unknowns: $\mu_a$ and $\mu_s$. The solution is given by:

$$\mu_a = \frac{3\omega}{c}\frac{k_r^2 - k_i^2}{2k_r k_i} \quad (21)$$

$$\mu'_s = \frac{c}{3\omega}2k_r k_i - \frac{3\omega}{c}\frac{k_r^2 - k_i^2}{2k_r k_i}$$

Having scanned the region of interest with the electromagnetic and acoustic waved and measured the intensity distribution of the scattered light, either a specific one of the above algorithms or the most general one is applied to the measured data to obtain a halftone pattern of the region of interest. If the most general algorithm is used, the real and imaginary parts of the coefficient $k^2$ can be retrieved, leading to the two equations, which determine the values of $\mu'_s$ and $\mu_a$.

Figure 7:
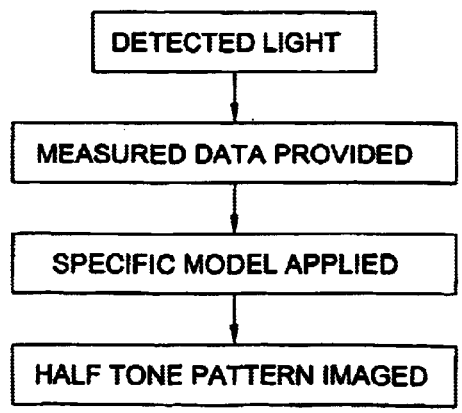
FIG. 7 illustrates a flow diagram of the main operational steps of the method according to the invention.

Thus, as shown in FIG. 7, to enable the imaging technique of the present invention, the measured data indicative of the distribution of the intensity of light scattered from the region of interest is provided. To this end, if the spatial distribution of the scattering coefficient in the region of interest is to be separately determined, the above-described technique of detecting scattered light using phase modulated electromagnetic radiation is employed. Then the measured data is processed by applying thereto a selected model (algorithm) in accordance with the source/detector arrangement (their number and respective positions), thereby determining the halftone pattern of the region of interest.

Figure 8A:
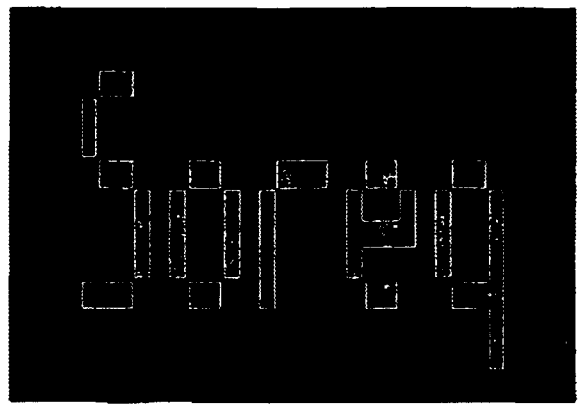
FIGS. 8A to 8C illustrate simulation results of applying the method of the present invention to obtain a halftone pattern of a region of interest in a scattering medium.
Figure 8B:
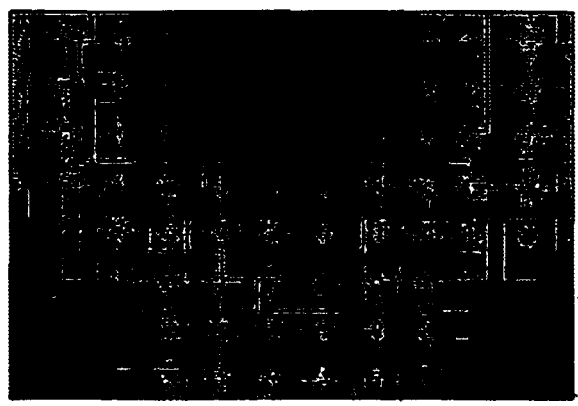
Figure 8C:

FIGS. 8A–8C illustrate the light tomography simulation results showing the advantageous features of the present invention. For simplicity, but without loss of generality, a 2D medium imaging is simulated. The medium shown in FIG. 8A is a two-dimensional slightly absorbing but scattering medium, and includes an absorbing pattern—the word "SOREQ" which is to be imaged. Simulated measurement data shown in FIG. 8B, is then processed by the technique of the present invention resulting in the halftone image of the absorbing pattern as shown in FIG. 8C. In this simulation, the above described case of the source and detector at the same location was used.

The simulation is performed as follow: light is injected in the medium (coordinate (16,0) in the picture) and the resulting image is simulated. In the simulation, the photons number in every volume element around r in the 2D medium is split as follows: $1-\exp[-\mu_a]$, is absorbed by the medium, and the rest is scattered evenly among its four nearest neighbors (rectangular grid). It should be noted that here $\mu_a$ is not exactly the absorption coefficient but is proportional to the absorption coefficient. The tagging process is simulated in the following manner: each photon that crosses the tagging zone is differentiated in the simulation and is counted separately when it reaches the detector.

It should be noted that the technique of the present invention does not require a three-dimensional acoustic scan of the entire body part containing the region of interest. It is possible to scan only a selected portion of the body, for example with high resolution ("zoom mode").

It should also be noted that by properly choosing the positions of the sources and detectors, it is possible to minimize the residual term $$\frac{1}{4}\left[\frac{\nabla \Gamma_s^{(1)}}{\Gamma_s^{(1)}} - \frac{\nabla \Gamma_d^{(1)}}{\Gamma_d^{(1)}}\right]^2.$$

This occurs for example when the sources and detectors are symmetrically arranged, for example, one-detector is located at the center of a polygon composed of sources.

The reconstruction technique of the present invention can be applied in cases that are different from imaging of biological tissues. The following two examples demonstrate the wide range of applications of this technique.

In the field of microscopy, for example aimed at examining multilayer printed circuit boards, high frequency (10 to 200 MHz) ultrasound transducers can be used so that the resolution is in the range of tens to hundreds of microns. By choosing the proper light wavelengths, different sorts of dielectric materials (i.e., having different absorbing patterns) can be identified in the different layers of the Printed Circuit Board, although their determination by ultrasonic methods only might be difficult. Such a microscopy can also be used for detecting melanoma and other skin lesions by analyzing the precise shape of the lesion in depth. It is an alternative to confocal microscopy or optical coherence tomography.

In a different context, the technique can be used for analyzing either the quality or the homogeneity of diffusive bulk-like materials such as food product or plastics, within their containers. To this end, laser light is coupled to the container (or directly to the material under evaluation), and an ultrasound pulse is scanned over the material. In the case of large containers (centimeters to meters), low frequency ultrasound can be used, which while reducing the resolution, increases the penetration depth and the scan speed. Having performed the reconstruction process of the present invention, a three-dimensional image of the absorption and/or scattering pattern can be obtained.

Those skilled in the art will readily appreciate that various modifications and changes can be applied to the embodiments of the invention as hereinbefore exemplified without departing from its scope defined in and by the appended claims.

What is claimed is:

1. A method of reconstructing an image of a region of interest inside a scattering medium, the method utilizing a map of distribution of the intensity of electromagnetic radiation components scattered from tagged locations within said region of interest, said map corresponding to certain relative positions of at least one source of the electromagnetic radiation (14) and at least one detector (16) of the scattered electromagnetic radiation with respect to one another and with respect to the tagged locations inside the medium the method being characterized in that:

data indicative of said relative positions of the at least one electromagnetic radiation source and that at least one scattered radiation detector is utilized to provide a mathematical model that presents a relation between a map of distribution of the intensity of electromagnetic radiation components γ scattered from tagged locations in a medium and a halftone map of an attenuation factor $\mu(r)$, which is a function of spatial variations of scattering and absorption coefficients of the mediums said relation being indicative of a degree of inhomogeneity of at least one of the scattering and absorption coefficients within the medium; and, said mathematical model is utilized for processing the map of the distribution of the electromagnetic radiation components to thereby obtain a halftone pattern of said region of interest.

2. The method according to claim 1, wherein said relation between the intensity distribution and the attenuation factor is based on the relative position of the at least one source of the electromagnetic radiation, the at least one detector and at least one acoustic radiation source used for tagging said locations in the medium as locations of interactions between the acoustic and electromagnetic radiation inside the medium.

3. The method according to claim 1, wherein said processing comprises determining changes in the intensity distribution of the electromagnetic radiation caused by an absorbing pattern in the region of interest, based on that said intensity for each location in the region of interest is related to the absorption coefficient and to the scattering properties of the medium defined by the electromagnetic propagation inside the medium.

4. The method according to claim 1, wherein said relation is determined as follows:

$$\frac{\nabla^2 \sqrt{\gamma}}{\sqrt{\gamma}} = -\frac{1}{4}\left[\frac{\nabla \Gamma_s}{\Gamma_s} - \frac{\nabla \Gamma_d}{\Gamma_d}\right]^2 + \mu^2(r_t)$$

wherein γ is the detected distribution of the intensity of the, electromagnetic radiation scattered from the tagged locations in the medium; $\Gamma_s$ and $\Gamma_d$ are probabilities of a photon to migrate from, respectively, the electromagnetic radiation source to the tagged location inside the medium and from the tagged location in the medium to the detector; and a $\mu(r_t)$ is the attenuation factor taken with respect to tagged locations $r_t$ in the medium.

5. The method according to claim 4, wherein the electromagnetic radiation source and the detector are at the same location, said relation being determined as follows:

$$\frac{\nabla^2 \sqrt{\gamma(r_t)}}{\sqrt{\gamma(r_t)}} = \mu^2(r_t).$$

6. The method according to claim 4, wherein the electromagnetic source and the detector are spaced from each other, and a certain angle θ therefore exists between central axes of incident and scattered light components propagating to and from an absorbing region in the medium, said relation being determined as follows:

$$\mu^2(r_t) = \frac{2}{1+\cos\theta} \frac{\nabla^2 \sqrt{\gamma}}{\sqrt{\gamma}}.$$

7. The method according to claim 4, wherein an array of the electromagnetic sources and an array of the detectors are used for obtaining the intensity distribution map, said relation being determined by an iterative algorithm comprising estimating detection by each of the detectors the scattering of the electromagnetic radiation produced by all the sources.

8. The method according to claim 1, comprising applying measurements to the medium to provide said the map of distribution of the intensity of electromagnetic radiation components scattered from the tagged locations within said region of interest.

9. The method according to claim 8, wherein the measurements are based on tagging the locations within said region of interest irradiated with the electromagnetic radiation.

10. The method according to claim 9, wherein sad tagging is based on interaction between the electromagnetic radiation with acoustic radiation inside the medium.

11. The method according to claim 10, wherein said tagging is applied to the amplitude of the scattered electromagnetic radiation component.

12. The method according to claim 10, wherein said tagging is applied to the amplitude and phase of the scattered electromagnetic radiation components.

13. The method according to claim 10, wherein said tagging comprises irradiating the region of interest with acoustic and electromagnetic waves to provide a plurality of locations inside the region of interest where the acoustic and electromagnetic waves interactive with each other, thereby affecting the parameters of the electromagnetic waves scattered from the region of interest in accordance with those of the acoustic waves, thereby enabling detection of the scattered electromagnetic waves with the affected parameters.

14. A processing device (32) for use with a measuring apparatus (10), which is operable to detect the intensity of light scattered from tagged locations in a scattering medium, the processing device comprising inter alia a memory utility (38) for storing data indicative of relative positions of at least one light source (14) and at least one detector (16) with respect to one another and with respect to the tagged locations inside the medium as used in said measuring apparatus, and comprising a data processing and analyzing utility (40) for processing input data and generating data indicative of the processing results, the processing device (32) being characterized in that:
said processing device is operable to utilize said data indicative of the relative positions to create a predetermined mathematical model and store it in the memory utility, said mathematical model presenting a relation between a map of the measured intensities distribution γ and a halftone map of a certain absorption factor $\mu(r)$, which is a function of the spatial variation of scattering and absorption coefficients of the medium, said relation being indicative of a degree of inhomogeneity of at least one of the scattering and absorption coefficients within the medium; and
said data processing and analyzing utility is responsive to input data coming from the measuring apparatus and being indicative of a map of distribution of the intensity of light scattered from the tagged locations within said region of interest, to apply said mathematical model to said measured data, and thereby obtain a halftone pattern of the region of interest.

15. The device according to claim 14, wherein said processing and analyzing utility operates to determine changes in the intensity distribution of the scattered light caused by an absorbing pattern in the region of interest, based on that said intensity for each the locations in the region of interest is related to the absorption coefficient and to the scattering properties of the medium defined by the light propagation inside the medium.

16. The device according to claim 14, wherein said relation between the intensity distribution and the attenuation factor is related to the relative position of the at least one light source, at least one detector for detecting the scattered radiation components, and at least one acoustic unit used for tagging said locations in the medium as locations of interactions between light and acoustic radiation in the medium.

17. The device according to claim 14, wherein said relation is determined as follows:

$$\frac{\nabla^2 \sqrt{\gamma}}{\sqrt{\gamma}} = -\frac{1}{4}\left[\frac{\nabla \Gamma_s}{\Gamma_s} - \frac{\nabla \Gamma_d}{\Gamma_d}\right]^2 + \mu^2(r_t)$$

wherein γ is the detected distribution of the intensity of light scattered from the tagged locations in the medium; $\Gamma_s$ and $\Gamma_d$ are probabilities of a photon to migrate from, respectively, the electromagnetic radiation source to the tagged location inside the medium and from the tagged location in the medium to the detector; and $\mu(r_t)$ is the attenuation factor taken with respect to tagged locations $r_t$ in the medium.

18. The device according to claim 17, wherein the light source and the detector are at the same location, said relation being determined as follows:

$$\frac{\nabla^2 \sqrt{\gamma(r_t)}}{\sqrt{\gamma(r_t)}} = \mu^2(r_t).$$

19. The device according to claim 17, wherein the light source and the detector are spaced from each other, and a certain angle θ therefore exists between central axes of incident and scattered light components propagating to and from an absorbing region in the medium, said relation being determined as follows:

$$\mu^2(r_t) = \frac{2}{1+\cos\theta}\frac{\nabla^2 \sqrt{\gamma}}{\sqrt{\gamma}}.$$

20. The device according to claim 17, wherein an array of the light sources and an array of the detectors are used for obtaining the intensity distribution map, said relation being determined by an iteractive algorithm comprising estimating detection by each of the detectors the light scattering produced by all the sources.

21. The device according to claim 14, and also comprising a processor connectable to the output of said meaning apparatus for receiving and analyzing data indicative of light components scattered from the medium to generate said measured data indicative of the map of distribution of the intensity of light components scattered from the tagged locations in the medium.

22. The device according to claim 14, being connectable to a processor associated with said measuring apparatus for receiving and analyzing data indicative of light components scattered from the region of interest to generate said measured data indicative of the map of distribution of the intensity of light components scattered from the tagged locations in the medium.

23. The device according to claim 14 and also comprising a measuring apparatus operable to measure electromagnetic radiation components scattered from tagged locations inside the region of interest, and generate measured data indicative of a map of distribution of the intensity of light scattered from the tagged locations within the region of interest.

24. The apparatus according to claim 23, wherein said measuring apparatus comprises: (i) an acoustic unit operable to transmit acoustic radiation to a plurality of locations in the medium, and a light source operable to illuminate said medium with incident light, to thereby produce light signals, being modulated in accordance with the acoustic radiation and allow detection of light components scattered from tagged locations of interactions between light and acoustic radiation inside the medium; and (ii) a detector unit operable to detect said modulated light signals and generate measured data indicative thereof, said measured data being in the form of a map of intensity distribution of light scattered from the locations inside the region of interest.

25. The apparatus according to claim 24, wherein the light source generates light of one or more wavelengths.

26. The apparatus according to claim 25, wherein said light source produces high-frequency modulated light components and said detector is modulated at a nearby high-frequency.

27. The apparatus according to claim 26, wherein said detector is associated with a phase system for detecting said modulated light sign and phase variations of the light components scattered from different locations in the region of interest, said map being indicative of the distribution of the scattering attenuation or within the locations inside the region of interest.

28. The apparatus according to claim 24, and also comprising a phase utility associated with the acoustic unit, thereby allowing for imaging of the region of interest along an axis of transmission of said acoustic radiation.

* * * * *